(12) United States Patent
Alba

(10) Patent No.: US 6,957,585 B2
(45) Date of Patent: Oct. 25, 2005

(54) THREAD WEAR GAUGE FOR COIL THREADS

(75) Inventor: Tony J. Alba, West Covina, CA (US)

(73) Assignee: CBC Industries, Inc., Pico Rivera, CA (US)

( * ) Notice: Subject to any disclaimer, the term of this patent is extended or adjusted under 35 U.S.C. 154(b) by 0 days.

(21) Appl. No.: 10/752,251

(22) Filed: Jan. 5, 2004

(65) Prior Publication Data

US 2004/0154406 A1 Aug. 12, 2004

Related U.S. Application Data

(60) Provisional application No. 60/438,690, filed on Jan. 7, 2003.

(51) Int. Cl.[7] .............................................. G01N 3/32
(52) U.S. Cl. ....................................................... 73/811
(58) Field of Search ......................... 73/811, 856, 859, 73/808, 809, 815; 33/199 R

(56) References Cited

U.S. PATENT DOCUMENTS

| 123,823 | A | | 2/1872 | Guard |
|---|---|---|---|---|
| 1,311,646 | A | | 7/1919 | Gordon |
| 2,662,300 | A | | 12/1953 | Foster |
| 3,195,278 | A | | 7/1965 | Ballou |
| 3,456,547 | A | | 7/1969 | Strong |
| 3,880,041 | A | | 4/1975 | Markowski et al. |
| 3,945,070 | A | | 3/1976 | Hauser |
| 4,185,391 | A | * | 1/1980 | Roley .......................... 33/563 |
| 4,309,135 | A | | 1/1982 | Gutshall |
| 4,519,144 | A | | 5/1985 | Larsen |
| 4,724,618 | A | | 2/1988 | Van Horssen |
| 5,490,333 | A | | 2/1996 | Nelson et al. |
| D421,575 | S | | 3/2000 | Palm |
| 6,289,595 | B1 | | 9/2001 | Galestien |

OTHER PUBLICATIONS

Gazanchan et al.(1989) Conical-screw-thread wear rate monitoring-by threaded template periodically on component and unscrewing template with force in opposite direction. (Derwent:Week 198917).*

* cited by examiner

Primary Examiner—Max Noori
(74) Attorney, Agent, or Firm—Bruce A. Jagger

(57) ABSTRACT

A thread wear gauge for coil threads. Coil threads have a nominal new thread profile that offers a substantial load bearing area. The thread wear gauge has a gauging thread with a silhouette that permits it to threadably engage with a coil thread that has been worn so that the shear load bearing area of the thread has been worn away from the coil thread to the point where the coil thread is unsafe for further use. The gauging thread will not threadably engage with the coil thread if the load bearing area has been worn to the point where it is unsafe. The thread wear gauge is a simple, reliable, hand held tool that is capable of being used under field conditions. In use, the thread wear gauge is grasped and manipulated with one hand. An attempt is made to threadably engage the gauging thread on the thread wear gauge with the coil thread that is to be tested. The operator observes whether the gauging thread threadably engages with the coil thread. If it does engage, use of the coil thread is discontinued. The thread wear gauge is equally applicable to internal and external coil threads, and also to concave and convex coil thread profiles.

11 Claims, 2 Drawing Sheets

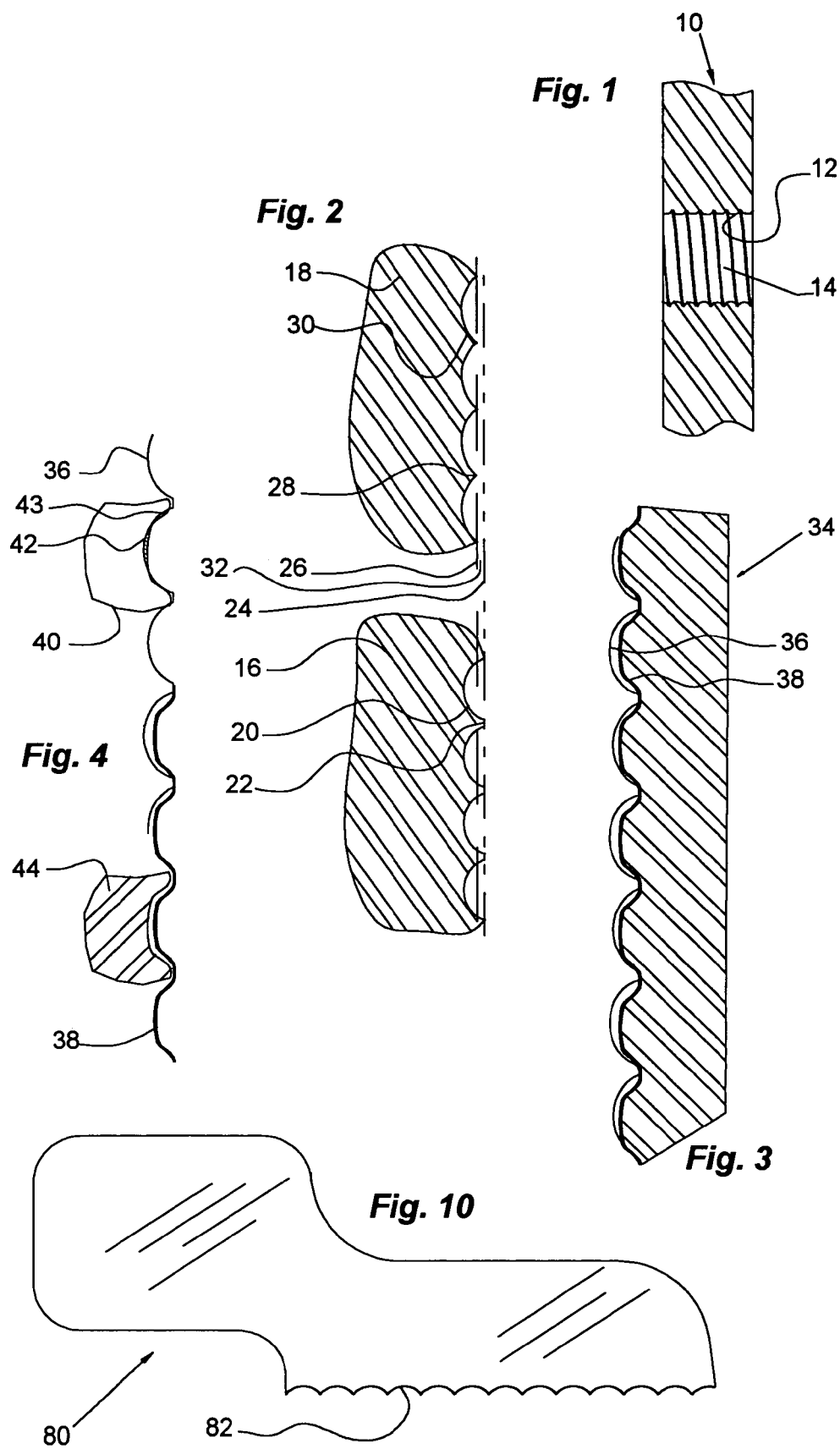

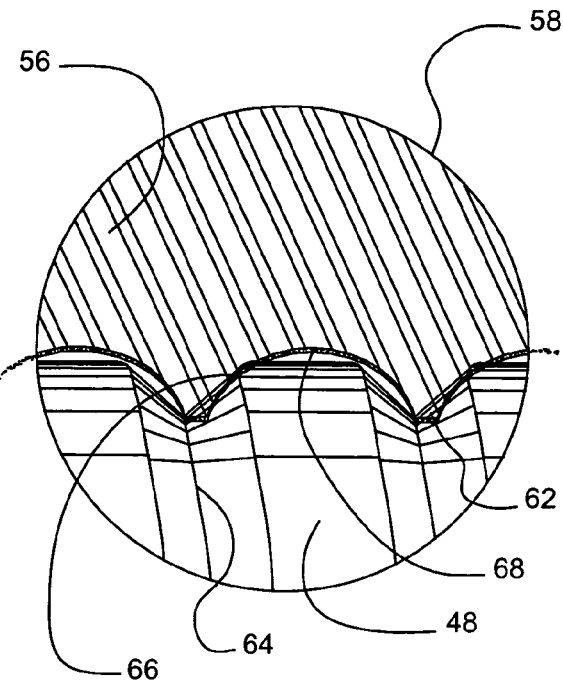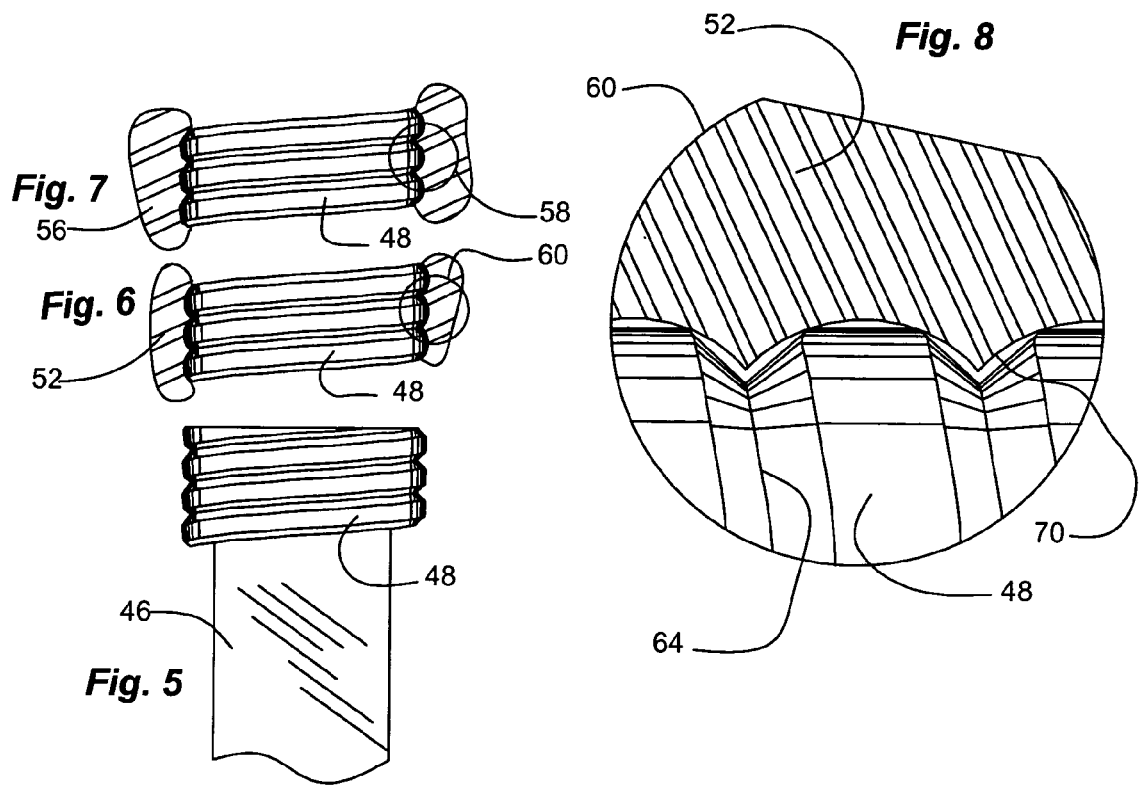

THREAD WEAR GAUGE FOR COIL THREADS

RELATED APPLICATION

This application claims the benefit of U.S. Provisional Application Ser. No. 60/438,690, filed Jan. 7, 2003.

BACKGROUND OF THE INVENTION

1. Field of the Invention

The invention relates in general to thread wear gauges, and, in particular, to thread wear gauges for user with coil threads.

2. Description of the Prior Art

Coil threads, sometimes known as "wire threads", are well known and widely used. See for example, Guard, U.S. Pat. No. 123,823, Gordon U.S. Pat. No. 1,311,646, Ballou U.S. Pat. No. 3,195,278, Strong U.S. Pat. No. 3,456,547, Hauser U.S. Pat. No. 3,945,070, and Gutshall U.S. Pat. No. 4,309,135. Coil threads are typically used in heavy duty construction applications where dirt, corrosion, and lack of lubrication cause substantial thread wear. In general, coil threads are not used in precision machine applications. Female coil threads, in the form of a coil of wire, are often cast into concrete where grit and a corrosive environment are inherently present. Threads with a coil thread profile are often used in other heavy construction equipment, such as steel street plates, and the like. Coil threads are very robust, and capable of functioning safely within a wide range of tolerances. Also, they remain functional even when the wear is uneven. Eventually, however, coil threads do wear out. When a coil thread in a piece of construction material, such as a steel street or road plate, becomes damaged to the point where it will no longer support the load for which it is rated, a serious safety problem may arise. Because coil threads remain functional throughout a wide range of tolerances, and the wear is frequently uneven, determining when a coil thread is too worn to be safe had been problematic, at least out in the field where it is impractical to use sophisticated testing equipment. Various thread gauges had previously been proposed, particularly as applied to machine screw threads. See, for example, Palm U.S. Pat. No. Des. 421,575 (a plate with male and female threads), Foster U.S. Pat. No. 2,662,300 (torque controlled go no-go plug gauge), Larsen U.S. Pat. No. 4,519,144 (a go no-go plug gauge with depth measuring capabilities), Van Horssen U.S. Pat. No. 4,724,618 (driver for a conventional plug gauge), Nelson U.S. Pat. No. 5,490,333 (adjustable three point roller thread ring gauge for external threads), Galestien U.S. Pat. No. 6,289,595 (machine for scanning a thread profile to determine thread geometry). The workers in this field had recognized the need for a simple, quick, and reliable way of determining when a coil thread, either male or female, has become worn beyond a safe limit.

These and other difficulties of the prior art have been overcome according to the present invention.

BRIEF SUMMARY OF THE INVENTION

A preferred embodiment of the thread wear gauge according to the present invention comprises a gauging thread (external or internal) which is sized and configured so that it will not threadably engage a coil thread that is to be tested for wear until the thread is worn beyond the safe limit.

Frequently, the changes in the major or minor diameters of a coil thread as it wears are small, generally in the order of less than 5 percent. It has been found that just measuring the changes in the diameters of a coil thread does not provide a reliable indication of the safety of the thread. The nominal new profile of a coil thread exhibits a substantial shear load bearing area. As a coil thread wears, the profile changes significantly from that of the nominal new profile. The shear load bearing area decreases as the thread profile changes with wear. According to the present invention, the gauging thread on a thread wear gauge is shaped so as to reliably and easily detect the change in profile that is associated with the degree of shear load bearing area loss that an unsafe thread exhibits. It has been found that a thread is generally worn beyond its safe limits when at least 30 percent, and preferably less than approximately 50 percent of the shear load bearing area is missing. Such a degree of wear can not be reliably detected by measuring the changes in the diameters of the thread. The diameters of the thread may be altered by only approximately 2 to 5 percent before the thread becomes unusable due to loss of bearing area. It is the change in the thread profile that reflects the changes in the shear load bearing area of the thread, rather than the changes in diameter that should be gauged. Safety is the main concern. For some applications safety is not compromised until approximately 50 percent of the load bearing area is gone. For other applications a loss of no more than approximately 30 percent of the shear load bearing area renders the thread unsafe for further use.

Other objects, advantages, and novel features of the present invention will become apparent from the following detailed description of the invention when considered in conjunction with the accompanying drawings.

BRIEF DESCRIPTION OF THE DRAWINGS

The present invention provides its benefits across a broad spectrum of commerce. While the description which follows hereinafter is meant to be representative of a number of such applications, it is not exhaustive. As those skilled in the art will recognize, the basic methods and apparatus taught herein can be readily adapted to many uses. It is applicant's intent that this specification and the claims appended hereto be accorded a breadth in keeping with the scope and spirit of the invention being disclosed despite what might appear to be limiting language imposed by the requirements of referring to the specific examples disclosed.

Referring particularly to the drawings for the purposes of illustration only and not limitation:

FIG. 1 is a cross-sectional view of a steel plate with an internally threaded bore wherein the thread is a new straight coil thread with a convex profile.

FIG. 2 is a fragmentary cross-sectional view of new and worn external coil threads arranged axially so as to illustrate, among other things, the diametrical differences between them.

FIG. 3 is a fragmentary cross-sectional view of a worn internal coil thread with the profile of a new internal coil thread superimposed on it to illustrate, among other things, the differences between them.

FIG. 4 is a view of the silhouette of a worn coil thread arranged axially with the profile of a new coil thread, and a fragmentary cross-sectional view of a coil thread wear gauge according to the present invention gaugingly positioned adjacent to the worn coil thread silhoutte, and a silhoutte of the same thread gauge gaugingly associated with the profile of the new coil thread to illustrate, among other things, the interpenetration that would be required for the thread gauge to threadably engage the new thread.

FIG. 5 is a fragmentary plan view of a coil thread wear gauge according to the present invention for an internal coil thread with a concave profile.

FIG. 6 is a fragmentary cross-sectional view of a worn internal concave coil thread gaugingly engaged with the coil thread wear gauge of FIG. 5 (see particularly FIG. 8) to illustrate, among other things, the application of the present invention to different thread profiles.

FIG. 7 is a fragmentary cross-sectional view of a new internal concave coil thread gaugingly engaged with the coil thread wear gauge of FIG. 5 to illustrate, among other things, the interpenetration of the gauge and workpiece (see particularly FIG. 9) that would be required for the gauge to threadably engage the new internal thread.

FIG. 8 is an enlarged view of the portion of FIG. 6 that is enclosed by circle 60.

FIG. 9 is an enlarged view of the portion of FIG. 7 that is enclosed by circle 58.

FIG. 10 is a plan view of an external coil thread wear gauge.

DETAILED DESCRIPTION OF THE PREFERRED EMBODIMENTS

The embodiments shown in FIGS. 1–9 illustrate

Referring now to the drawings wherein like reference numerals designate identical or corresponding parts throughout the several views there is illustrated generally at 10 a workpiece with bore 14 extending therethrough and an internal coil thread 12 therein. Coil thread 12 is a conventional new internal coil thread of convex form. The load bearing surfaces are convex in form. The mating external thread, not shown, is concave in profile. That is, the load bearing surfaces on the mating external thread are concave in form.

The embodiment of FIG. 2 illustrates an external coil thread in both the new and worn conditions aligned on a common central axis, not shown. An externally threaded workpiece is illustrated in fragmentary cross-section at 16. The thread on workpiece 16 is illustrated in its nominal new thread profile. A typical concave load bearing surface is illustrated at 20. There is a helical land 22 of significant axial length between the load bearing surfaces. Land 22 permits the concave load bearing surface to wear to a considerable degree before there is any reduction in the diameter of the thread. A workpiece 18 with an identical coil thread that has been worn beyond its safe limit has a load bearing surface illustrated at 30. The heilical land has been worn away in workpiece 18 until only a helical pointed ridge 28 remains between the load bearing surfaces. The load bearing surfaces have been elongated and reduced in area. Also, the angles at which the load bearing surfaces extend have been altered so that they are generally more shallow than in the corresponding new thread. This change in angles is also believed to negatively influence the safety of the thread. Line 24 illustrates the location of the radial outer edge of axially extending land 22, and line 26 shows the location of the radially outer pointed tip of helical ridge of 28. The wear of the thread in workpiece 18 has progressed beyond the point where the land 22 has disappeared. Part of the load bearing wall 30 has been worn away. The diameter of the thread on workpiece 18 is smaller than the corresponding thread on workpiece 16 by a small amount, typically 3 to 5 percent, as indicated at 32. The area of the convex load bearing surface indicated at 30 is, however, only approximately half of that exhibited by the new thread at 20. The silhouette of the worn thread on workpiece 18 is shown for purposes of illustration as being worn in a regular pattern. In use, the wear on the threads is typically somewhat irregular, so to be reliable a thread wear gauge must accommodate such irregular wear. Because of the reduction in diameter that occurs when the helical land has been completely worn or eroded away, a thread wear gauge with an internal gauging thread should preferably have a diameter that is smaller than the diameter of the nominal new thread. Thus, the workpiece 16 can not be threaded into the thread wear gauge. The most significant part of the profile of the thread wear gauge is, however, in a configuration that permits the detection of the loss of load bearing area. That is, even if the diameter of the gauging thread is such that new thread on workpiece 16 can engage it, the profile of the gauging thread does not permit such engagement.

FIG. 3 illustrates a workpiece 34 in fragmentary cross-section with a worn internal coil thread having the approximate silhouette indicated at 38. The nominal new profile of the same thread is indicated at 36. There is a substantial change that occurs in the shape of the thread as it wears. A substantial amount (approximately half) of the load bearing area of the thread is worn away, and the angles of contact have shallowed until the thread as indicated at 38 becomes unsafe.

FIG. 4 illustrates a thread wear gauge 44 (shown for clarity of illustration in fragmentary cross-section) with an external gauging thread in gauging engagement with worn thread 38. Worn thread silhouette 38, nominal new thread profile 36, thread wear gauge 44, and thread wear gauge silhouette 40 are all arranged on a common longitudinal axis, not shown. There is a substantial amount of clearance between the gauging thread of thread gauge 44 and the worn thread 38. There is enough clearance to accommodate uneven wear of thread 38, and still threadably engage the worn internal thread 38. A silhouette 40 of thread wear gauge 44 is shown in association with the nominal new thread 36. The illustrated engagement between the new thread 36 and the gauging thread could not occur because the gauging thread and the new thread would be required to interpenetrate one another. The areas of interpenetration are illustrated, for example, at 42 and 43. The thread gauge 40 is shown in silhouette so as to more clearly illustrate the impermissible interpenetration. Thread gauge 44 can not be threadably engaged with a thread until that thread is worn beyond its safe limit. That wear occurs both in reduction of the load bearing area by approximately half, and in a shallowing of the angles of the load bearing surfaces. The contact between threadably engaged threads is thus both reduced and weakened.

The embodiment of FIG. 5 illustrates a thread wear gauge 46 with a helical gauging thread 48 having an external convex thread form. Gauging thread 48 is adapted to gaugingly engage a worn internal coil thread with a concave thread profile. The concave thread profile is reversed as between the external and internal threads as compared with the embodiments of FIGS. 1–4.

The embodiment of FIG. 6 illustrates a worn internal coil thread in workpiece 52 engaged in threadable relationship with guaging thread 48. The details of the engagement between the worn thread in workpiece 52 and gauging thread 48 are shown in more detail in FIG. 8. FIG. 8 is an enlarged view of the area enclosed by 60 in FIG. 6. The profile of the worn internal thread is illustrated at 70. The minor diameter 64 of the gauging thread 48 is significantly less than the major diameter of the worn thread so that variations in the diameter of the thread in the workpiece 52 due to uneven wear do not impair the reliability of the indications of wear given by gauging thread 48. The axial breadth of gauging thread 48 is such that it will not threadably engage with worn thread 70 until the axially extending lands of the thread have been worn to a sharply pointed ridge as shown in FIG. 8. When this condition of wear develops, the load bearing area has been reduced to approximately half of that offered by the thread when it was new.

FIG. 7 is similar to FIG. 6, and FIG. 9 is similar to FIG. 8. FIGS. 7 and 9 illustrate the impermissible interengagement that occurs when a new thread 68 in workpiece 56 is threadably engaged with gauging thread 48. In the enlarged area bounded by 58, the new thread profile has been shown for the purpose of illustration as being filled. This serves to visually distinguish the profile of the new thread from the other lines in FIG. 9. Impermissible interpenetration between the gauging thread 48 and the new thread 68 is apparent, for example, at 62 and 66. Gauging thread 48 could not be threadably engaged with new thread 68 because of this interpenetration. Most of the interpenetration is due to the presence of the material that provides the axially extending lands in the new thread. The wearing away of this material is believed to be the main contributor to the failure of the thread.

FIG. 10 is illustrative of, for example, a coil thread wear gauge 80. The thread profile 82 indicates when an external coil thread has worn to the point where it is no longer safe.

What have been described are preferred embodiments in which modifications and changes may be made without departing from the spirit and scope of the accompanying claims. Clearly, many modifications and variations of the present invention are possible in light of the above teachings. It is therefore to be understood that, within the scope of the appended claims, the invention may be practiced otherwise than as specifically described.

What is claimed is:

1. A thread wear gauge for gauging when a straight coil thread having a nominal new thread profile has been worn beyond safe limits, said nominal new thread profile providing said straight coil thread with a shear load bearing area, said thread wear gauge comprising:
   a gauging thread, said gauging thread being adapted to threadably engage said straight coil thread wherein at least enough of said shear load bearing area has worn away to render said straight coil thread unsafe for continued use, said gauging thread adapted to being unable to threadably engage with said straight coil thread when said straight coil thread is safe for continued use.

2. A thread wear gauge of claim 1 wherein said straight coil thread is an internal thread.

3. A thread wear gauge of claim 1 wherein said straight coil thread is an external thread.

4. A thread wear gauge of claim 1 wherein said straight coil thread is internal and said nominal new thread profile is convex.

5. A thread wear gauge of claim 1 wherein said straight coil thread is internal and said nominal new thread profile is concave.

6. A thread wear gauge of claim 1 wherein said gauging thread being adapted to threadably engage said straight coil thread wherein at least approximately 30 percent of said shear load bearing area has been worn away to render said straight coil thread unsafe for continued use.

7. A thread wear gauge of claim 1 wherein said gauging thread being adapted to threadably engage said straight coil thread wherein at least approximately 50 percent of said shear load bearing area has been worn away to render said straight coil thread unsafe for continued use.

8. A method for gauging when a straight coil thread having a nominal new thread profile has been worn beyond safe limits using a thread wear gauge, said nominal new thread profile providing said straight coil thread with a load bearing area, said method comprising:
   selecting a thread wear gauge having a gauging thread, said gauging thread being adapted to threadably engage said straight coil thread wherein at least approximately half of said load bearing area has worn away, and said gauging thread adapted to being unable to threadably engage with said straight coil thread when less than approximately half of said load bearing area has been worn away;
   attempting to threadably engage said gauging thread with said straight coil thread;
   observing whether said gauging thread can be threadably engaged with said straight coil thread; and
   discontinuing the use of said straight coil thread if said gauging thread can be threadably engaged with said straight coil thread.

9. A thread wear gauge for gauging when a straight coil thread having a nominal new thread profile has been worn beyond safe limits, said nominal new thread profile providing said straight coil thread with a shear load bearing area, said thread wear gauge comprising:
   a gauging thread, said gauging thread being adapted to threadably engage said straight coil thread wherein at least approximately thirty percent of said shear load bearing area has worn away, said gauging thread adapted to being unable to threadably engage with said straight coil thread when less than approximately thirty percent of said shear load bearing area has been worn away.

10. A thread wear gauge of claim 9 wherein said gauging thread being adapted to being unable to threadably engage with said straight coil thread when less than approximately fifty percent of said shear load bearing area has been worn away.

11. A method for gauging when a straight coil thread having a nominal new thread profile has been worn beyond safe limits using a thread wear gauge, said nominal new thread profile providing said straight coil thread with a shear load bearing area, said method comprising:
   selecting a thread wear gauge having a gauging thread, said gauging thread being adapted to threadably engage said straight coil thread wherein at least approximately thirty percent of said shear load bearing area has worn away, and said gauging thread adapted to being unable to threadably engage with said straight coil thread when less than approximately thirty percent of said shear load bearing area has been worn away;
   attempting to threadably engage said gauging thread with said straight coil thread;
   observing whether said gauging thread can be threadably engaged with said straight coil thread; and
   discontinuing the use of said straight coil thread if said gauging thread can be threadably engaged with said straight coil thread.

* * * * *